United States Patent
Peng et al.

(10) Patent No.: US 10,611,709 B2
(45) Date of Patent: Apr. 7, 2020

(54) LIQUID PHASE PROCESS FOR PREPARING (E)-1,1,1,4,4,4-HEXAFLUOROBUT-2-ENE

(71) Applicant: The Chemours Company FC, LLC, Wilmington, DE (US)

(72) Inventors: Sheng Peng, Hockessin, DE (US); Andrew Jackson, Newark, DE (US); Stephan Brandstadter, Philadelphia, PA (US); Mario Joseph Nappa, Newark, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 16/126,560

(22) Filed: Sep. 10, 2018

(65) Prior Publication Data

US 2019/0077733 A1   Mar. 14, 2019

Related U.S. Application Data

(60) Provisional application No. 62/556,744, filed on Sep. 11, 2017.

(51) Int. Cl.

| | |
|---|---|
| *C07C 17/25* | (2006.01) |
| *B01J 23/745* | (2006.01) |
| *B01J 27/10* | (2006.01) |
| *B01J 27/135* | (2006.01) |
| *B01J 31/02* | (2006.01) |
| *C07C 17/20* | (2006.01) |
| *C07C 19/12* | (2006.01) |
| *C07C 21/185* | (2006.01) |

(52) U.S. Cl.
CPC ............ *C07C 17/25* (2013.01); *B01J 23/745* (2013.01); *B01J 27/10* (2013.01); *B01J 27/135* (2013.01); *B01J 31/0239* (2013.01); *B01J 31/0268* (2013.01); *C07C 17/206* (2013.01); *C07C 19/12* (2013.01); *C07C 21/185* (2013.01); *B01J 2531/98* (2013.01)

(58) Field of Classification Search
CPC ..... C07C 17/206; C07C 17/25; C07C 17/278; C07C 17/358; C07C 21/18; C07C 19/10; C07B 2200/09
See application file for complete search history.

(56) References Cited

U.S. PATENT DOCUMENTS

| 8,461,401 B2 | 6/2013 | Tung et al. |
| 2007/0152200 A1 | 7/2007 | Hedrick et al. |
| 2011/0237844 A1 | 9/2011 | Tung et al. |
| 2014/0303410 A1* | 10/2014 | Swearingen .......... C07C 17/206 570/134 |
| 2017/0015607 A1 | 1/2017 | Baldychev et al. |
| 2018/0264303 A1* | 9/2018 | Robin ................. A62D 1/0092 |

FOREIGN PATENT DOCUMENTS

| CN | 103 172 489 | 7/2015 |
| WO | WO 2013/062733 | 5/2013 |
| WO | WO 2016/078225 | 5/2016 |

OTHER PUBLICATIONS

Ye et al (CN103172489 machine translation), Jun. 2013.*
International Search Report and Written Opinion in International Application No. PCT/US2018/050229, dated Nov. 20, 2018, 13 pages.

* cited by examiner

*Primary Examiner* — Jafar F Parsa

(57) ABSTRACT

Disclosed herein are methods of producing E-$CF_3CH$=$CHCF_3$ in a liquid phase. Also disclosed are methods of preparing $CF_3CH_2CHClCF_3$ and $CF_3CHClCH_2CCl_3$.

24 Claims, No Drawings

LIQUID PHASE PROCESS FOR PREPARING (E)-1,1,1,4,4,4-HEXAFLUOROBUT-2-ENE

CROSS-REFERENCE TO RELATED APPLICATIONS

This application claims the benefit of U.S. Provisional Application Ser. No. 62/556,744, filed Sep. 11, 2017, the disclosure of which is incorporated herein by reference in its entirety.

FIELD OF THE INVENTION

The disclosure herein relates to a liquid phase process for preparing (E)-1,1,1,4,4,4-hexafluorobut-2-ene (E-CF$_3$CH=CHCF$_3$) from CF$_3$CH$_2$CHClCF$_3$. The disclosure herein further provides methods of preparing CF$_3$CH$_2$CHClCF$_3$ and CF$_3$CHClCH$_2$CCl$_3$.

BACKGROUND OF THE INVENTION

Various types of polyurethane foams require blowing (expansion) agents for their manufacture. Historically, polyurethane foams used CFCs (chlorofluorocarbons) and HCFCs (hydrochlorofluorocarbons) as the primary blowing agents. CFCs have fallen into disfavor due to the implication of chlorine-containing molecules in the destruction of stratospheric ozone. Further, the production and use of CFCs has been restricted by the Montreal Protocol. HCFCs have been proposed as CFC substitutes, and are currently employed as foam blowing agents. However, HCFCs have also been shown to contribute to the depletion of stratospheric ozone, and as a result their use has come under scrutiny. The widespread use of HCFCs is scheduled for eventual phase out under the Montreal Protocol.

Hydrofluoroolefins (HFOs) represent a class of compounds being used as blowing agents in polyurethane and related foams that have a low global warming potential. Processes for the manufacture of HFOs have been previously described (e.g., U.S. Pat. Publ. No. 2007/152200 describes fire extinguishing and fire suppression compositions comprising unsaturated fluorocarbons and methods of preparing the HFOs). U.S. Pat. No. 8,461,401 describes a method for making haxafluoro-2-butene (HFO-1336). However, this method suffers from yield loss when performed in the liquid phase. To minimize yield loss in the first step of the process, a vapor phase process is employed. The overall process involves one liquid phase step and two gas phase steps. The cost for employing gas phase reactors can be high.

Thus, there is a need for a process for preparing HFOs, particularly HFO-1336, that reduces costs yet results in improved yields. There is also a need for a process for preparing HFOs that can be done in one phase, for example, the liquid phase.

INCORPORATION BY REFERENCE

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

SUMMARY OF THE INVENTION

Provided herein is a liquid phase process for preparing (E)-1,1,1,4,4,4-hexafluorobut-2-ene (E-CF$_3$CH=CHCF$_3$; E-1336mzz). The process provided herein comprises treating CF$_3$CH$_2$CHClCF$_3$ (346mdf) with an effective amount of a base to form a mixture comprising the E-CF$_3$CH=CHCF$_3$, wherein the process is a liquid phase process. In some embodiments, the mixture comprises E-CF$_3$CH=CHCF$_3$ and one or more of hexafluoroisobutylene (1336mt), 1,1,1,4,4,4-hexafluorobutane (356mff), (E)-1-chloro-1,1,4,4,4-pentafluorobut-2-ene (1335lzz), and Z—CF$_3$CH=CHCF$_3$.

In some embodiments, the base is selected from the group consisting of lithium hydroxide, lithium oxide, sodium hydroxide, sodium oxide, potassium hydroxide, potassium oxide, rubidium hydroxide, rubidium oxide, cesium hydroxide, cesium oxide, calcium hydroxide, calcium oxide, strontium hydroxide, strontium oxide, barium hydroxide, and barium oxide. In some embodiments, the base is potassium hydroxide. In some embodiments, the base is sodium hydroxide. In some embodiments, the base is in an aqueous solution. In some embodiments, the concentration of base in the aqueous solution is from about 4M to about 12 M.

In some embodiments, the process is performed in the presence of a phase transfer catalyst. In some embodiments, the phase transfer catalyst is selected from the group consisting of a quaternary ammonium salt, a heterocyclic ammonium salt, an organic phosphonium salt, and a non-ionic compound. In some embodiments, the phase transfer catalyst is selected from the group consisting of benzyltrimethylammonium chloride, benzyltriethylammonium chloride, methyltricaprylammonium chloride, methyltributylammonium chloride, methyltrioctylammonium chloride, dimethyldiphenylphosphonium iodide, methyltriphenoxyphosphonium iodide, tetrabutylphosphonium bromide, tetrabutylphosphonium chloride, hexadecyltributylphosphonium bromide, and DL-α-tocopherol methoxypolyethylene glycol succinate. In some embodiments, the phase transfer catalyst is methyltrioctylammonium chloride.

In some embodiments of the process provided herein, the base is sodium hydroxide and the phase transfer catalyst is methyltrioctylammonium chloride.

In some embodiments of the process provided herein, the mixture further comprises one or more of hexafluoroisobutylene (1336mt), 1,1,1,4,4,4-hexafluorobutane (356mff), (E)-1-chloro-1,1,4,4,4-pentafluorobut-2-ene (1335lzz), and Z—CF$_3$CH=CHCF$_3$. In some embodiments, the E-CF$_3$CH=CHCF$_3$ is produced in a yield of about 95% or greater. In some embodiments, the E-CF$_3$CH=CHCF$_3$ is produced with a selectivity of about 99 mol % or greater with respect to other components of the mixture.

In some embodiments of the process provided herein, the E-CF$_3$CH=CHCF$_3$ is substantially isolated from the mixture.

In some embodiments, the process comprises preparing CF$_3$CH$_2$CHClCF$_3$ (346mdf). In some embodiments, CF$_3$CH$_2$CHClCF$_3$ is prepared according to a second process comprising contacting CF$_3$CHClCH$_2$CCl$_3$ (343jfd) with HF in the presence of a catalyst, wherein the second process is a liquid phase process.

In some embodiments, the catalyst is a metal halide. In some embodiments, the metal halide is selected from the group consisting of SbF$_5$, SbCl$_5$, SbCl$_3$, SnCl$_4$, TaCl$_5$, TiCl$_4$, NbCl$_5$, MoCl$_6$, WCl$_6$, antimony (V) chlorofluorides, and combinations thereof. In some embodiments, the metal halide is SbF$_5$. In some embodiments, the metal halide is TaCl$_5$. In some embodiments, the metal halide is antimony (V) chlorofluorides.

In some embodiments, the second process is performed at a temperature of from about 50° C. to about 100° C.

In some embodiments, the $CF_3CH_2CHClCF_3$ is produced in a yield of about 93% or greater. In some embodiments, the $CF_3CH_2CHClCF_3$ is produced in a yield of about 95% or greater.

In some embodiments, the process comprises preparing $CF_3CHClCH_2CCl_3$ (343jfd). In some embodiments, $CF_3CHClCH_2CCl_3$ is prepared according to a third process comprising contacting carbon tetrachloride with 3,3,3-trifluoropropene in the presence of an organophosphorus compound and a catalyst comprising a metal, wherein the third process is a liquid phase process.

In some embodiments, the organophosphorus compound is selected from the group consisting of a phosphate ester, a phosphate amide, a phosphonic acid, a phosphonic ester, a phosphinic acid, a phosphinic ester, a phosphine oxide, a phosphine imide, a phosphonium salt, a phosphorene, a phosphite, a phosphonate, a phosphinite, and a phosphine. In some embodiments, the organophosphorus compound is selected from the group consisting of a phosphate, a diphosphate, a triphosphate, and a trialkylphosphate. In some embodiments, the organophosphorus compound is tributylphosphate.

In some embodiments, the metal of the catalyst is selected from the group consisting of Fe, Co, Ni, Cu, Mo, Cr, and Mn. In some embodiments, the metal is Fe.

In some embodiments, the third process takes place at a temperature of from about 100° C. to about 120° C.

Provided herein is a process for preparing $E\text{-}CF_3CH=CHCF_3$, comprising: (a) contacting carbon tetrachloride with 3,3,3-trifluoropropene in the presence of an organophosphorus compound and a catalyst comprising a metal to produce $CF_3CHClCH_2CCl_3$; (b) contacting the $CF_3CHClCH_2CCl_3$ with HF in the presence of a catalyst to produce $CF_3CH_2CHClCF_3$; and (c) treating the $CF_3CH_2CHClCF_3$ with an effective amount of a base to form a mixture comprising the $E\text{-}CF_3CH=CHCF_3$, wherein the process is a liquid phase process. In some embodiments, step (c) is performed in the presence of a phase transfer catalyst. In some embodiments, the mixture further comprises one or more of hexafluoroisobutylene (1336mt), 1,1,1,4,4,4-hexafluorobutane (356mff), (E)-1-chloro-1,1,4,4,4-pentafluorobut-2-ene (1335lzz), and $Z\text{—}CF_3CH=CHCF_3$. In some embodiments, the $E\text{-}CF_3CH=CHCF_3$ is substantially isolated from the mixture.

Provided herein is a process for preparing $E\text{-}CF_3CH=CHCF_3$, comprising: (a) contacting carbon tetrachloride with 3,3,3-trifluoropropene in the presence of an organophosphorus compound and a catalyst comprising a metal to produce $CF_3CHClCH_2CCl_3$; (b) contacting the $CF_3CHClCH_2CCl_3$ with HF in the presence of a catalyst to produce $CF_3CH_2CHClCF_3$; and (c) treating the $CF_3CH_2CHClCF_3$ with an effective amount of a base in the presence of a phase transfer catalyst to form a mixture comprising the $E\text{-}CF_3CH=CHCF_3$, wherein the process is a liquid phase process. In some embodiments, the base of step (c) is sodium hydroxide. In some embodiments, the mixture further comprises one or more of hexafluoroisobutylene (1336mt), 1,1,1,4,4,4-hexafluorobutane (356mff), (E)-1-chloro-1,1,4,4,4-pentafluorobut-2-ene (1335lzz), and $Z\text{—}CF_3CH=CHCF_3$. In some embodiments, the $E\text{-}CF_3CH=CHCF_3$ is substantially isolated from the mixture.

Also provided herein is a composition comprising: (a) $E\text{-}CF_3CH=CHCF_3$, and (b) one or more additional compounds selected from the group consisting of hexafluoroisobutylene (1336mt), 1,1,1,4,4,4-hexafluorobutane (356mff), (E)-1-chloro-1,1,4,4,4-pentafluorobut-2-ene (1335lzz), and $Z\text{—}CF_3CH=CHCF_3$, wherein the composition comprises greater than about 99 mol % $E\text{-}CF_3CH=CHCF_3$.

Also provided herein is a composition prepared according to the process described herein, comprising: (a) $E\text{-}CF_3CH=CHCF_3$, and (b) one or more additional compounds selected from the group consisting of hexafluoroisobutylene (1336mt), 1,1,1,4,4,4-hexafluorobutane (356mff), (E)-1-chloro-1,1,4,4,4-pentafluorobut-2-ene (1335lzz), and $Z\text{—}CF_3CH=CHCF_3$, wherein the composition comprises greater than about 99 mol % $E\text{-}CF_3CH=CHCF_3$.

Other objects and advantages will become apparent to those skilled in the art upon reference to the detailed description that hereinafter follows.

DETAILED DESCRIPTION OF THE INVENTION

The hydrofluoroolefin (E)-1,1,1,4,4,4-hexafluorobut-2-ene ($E\text{-}CF_3CH=CHCF_3$; E-1336mzz) is a blowing agent with low global warming potential. Provided herein is a process for preparing $E\text{-}CF_3CH=CHCF_3$ (E-1336mzz). The process is a liquid phase process comprising the steps of:
(a) contacting carbon tetrachloride with 3,3,3-trifluoropropene in the presence of an organophosphorus compound and a catalyst comprising a metal to produce $CF_3CHClCH_2CCl_3$ (343jfd);
(b) contacting the $CF_3CHClCH_2CCl_3$ (343jfd) with HF in the presence of a catalyst to produce $CF_3CH_2CHClCF_3$ (346mdf); and
(c) treating the $CF_3CH_2CHClCF_3$ (346mdf) with an effective amount of a base to form a mixture comprising the $E\text{-}CF_3CH=CHCF_3$ (E-1336mzz).

In some embodiments, step (c) is performed in the presence of a phase transfer catalyst.

In some embodiments, the $E\text{-}CF_3CH=CHCF_3$ (E-1336mzz) is substantially isolated from the mixture.

Step (a)—Production of $CF_3CHCl CH_2CCl_3$ (343jfd)

In step (a), carbon tetrachloride is reacted with 3,3,3-trifluoropropene in the presence of an organophosphorus compound and a catalyst comprising a metal to produce 2,4,4,4-tetrachloro-1,1,1-trifluorobutane ($CF_3CHClCH_2CCl_3$; 343jfd). Reacting carbon tetrachloride with 3,3,3-trifluoropropene is carried out in a liquid phase.

In some embodiments, the organophosphorus compound of step (a) is a phosphate ester, a phosphate amide, a phosphonic acid, a phosphonic ester, a phosphinic acid, a phosphinic ester, a phosphine oxide, a phosphine imide, a phosphonium salt, a phosphorene, a phosphite, a phosphonate, a phosphinite, or a phosphine. In some embodiments, the organophosphorus compound is a phosphate, a diphosphate, a triphosphate, or a trialkylphosphate. In some embodiments, the organophosphorus compound is tributylphosphate.

In some embodiments, the organophosphorus compound of step (a) comprises between about 0.1% and about 5% by weight of the reaction mixture composition of step (a). For example, about 0.5% to about 2.5%, or about 1% to about 1.5% by weight of the reaction mixture composition of step (a).

In some embodiments, the metal of the catalyst of step (a) is iron (Fe), cobalt (Co), nickel (Ni), copper (Cu), molybdenum (Mo), chromium (Cr), or manganese (Mn). In some embodiments, the metal is iron. In some embodiments, the catalyst comprising a metal is iron powder.

In some embodiments, the catalyst comprising a metal of step (a) comprises between about 0.01% and about 1% by weight of the reaction mixture composition of step (a). For example, about 0.1% to about 0.7%, or about 0.3% to about 0.6% by weight of the composition. In some embodiments, the catalyst comprising a metal comprises about 0.5% by weight of the reaction mixture composition of step (a).

In some embodiments, the carbon tetrachloride can be present in the reaction mixture composition of step (a) in an amount of about 50% to about 90% by weight of the composition. For example, about 55% to about 85%, about 60% to about 80%, about 65% to about 75%, or about 68% to about 72% by weight of the reaction mixture composition of step (a).

In some embodiments, the 3,3,3-trifluoropropene can be present in the reaction mixture composition of step (a) in an amount of about 10% to about 50% by weight of the composition. For example, about 15% to about 45%, about 20% to about 40%, about 25% to about 35%, or about 28% to about 32% by weight of the reaction mixture composition of step (a).

In some embodiments, reacting carbon tetrachloride in a liquid phase with 3,3,3-trifluoropropene in the presence of an organophosphorus compound and a catalyst comprising a metal to produce $CF_3CHClCH_2CCl_3$ (343jfd) is performed at a temperature of about 90° C. to about 130° C., about 100° C. to about 120° C., or about 105° C. to about 115° C. In some embodiments, reacting carbon tetrachloride in a liquid phase with 3,3,3-trifluoropropene in the presence of an organophosphorus compound and a catalyst comprising a metal to produce $CF_3CHClCH_2CCl_3$ (343jfd) is performed at a temperature of about 90° C., 95° C., 100° C., 105° C., 110° C., 115° C., 120° C., 125° C., or about 130° C.

In some embodiments, reacting carbon tetrachloride in a liquid phase with 3,3,3-trifluoropropene in the presence of an organophosphorus compound and a catalyst comprising a metal to produce $CF_3CHClCH_2CCl_3$ (343jfd) is performed for a time of about 1 hour to about 10 hours or about 2 hours to about 5 hours. In some embodiments, reacting carbon tetrachloride in a liquid phase with 3,3,3-trifluoropropene in the presence of an organophosphorus compound and a catalyst comprising a metal to produce $CF_3CHClCH_2CCl_3$ (343jfd) is performed for a time of about 1 hour, 2 hours, 3 hours, 4 hours, 5 hours, 6 hours, 7 hours, 8 hours, 9 hours, or about 10 hours.

Reacting carbon tetrachloride in a liquid phase with 3,3,3-trifluoropropene in the presence of an organophosphorus compound and a catalyst comprising a metal to produce $CF_3CHClCH_2CCl_3$ (343jfd) can be performed at a temperature of about 90° C. to about 130° C., about 100° C. to about 120° C., or about 105° C. to about 115° C. for a time of about 1 hour to about 10 hours or about 2 hours to about 5 hours. In some embodiments, reacting carbon tetrachloride in a liquid phase with 3,3,3-trifluoropropene in the presence of an organophosphorus compound and a catalyst comprising a metal to produce $CF_3CHClCH_2CCl_3$ (343jfd) is performed at temperature of about 105° C. to about 115° C. for a time of about 2 hours to about 5 hours. In some embodiments, reacting carbon tetrachloride in a liquid phase with 3,3,3-trifluoropropene in the presence of an organophosphorus compound and a catalyst comprising a metal to produce $CF_3CHClCH_2CCl_3$ (343jfd) is performed at temperature of about 110° C. for a time of about 3 hours.

In some embodiments, the $CF_3CHClCH_2CCl_3$ (343jfd) is isolated prior to step (b). In some embodiments, $CF_3CHClCH_2CCl_3$ (343jfd) is isolated with a purity of greater than about 90%, 92%, 94%, 96%, or greater than about 98%. In some embodiments, the purity is determined by chromatography. In some embodiments, the purity is determined by gas chromatography (GC) analysis.

In some embodiments, about 95% or greater of the 3,3,3-trifluoropropene is converted to $CF_3CHClCH_2CCl_3$ (343jfd). For example, about 95%, 96%, 97%, 98%, 99%, or 100% of the 3,3,3-trifluoropropene is converted to $CF_3CHClCH_2CCl_3$ (343jfd). In some embodiments, $CF_3CHClCH_2CCl_3$ (343jfd) is produced with a selectivity of about 80 mol % to about 100 mol %, or about 85 mol % to about 95 mol %, or about 87 mol % to about 90 mol %, with respect to other components of the mixture.

Step (b)—Production of $CF_3CH_2CHClCF_3$ (346mdf)

In step (b), $CF_3CHClCH_2CCl_3$ (343jfd) is treated with hydrogen fluoride (HF) in the presence of a catalyst to produce 2-chloro-1,1,1,4,4,4-hexafluorobutane ($CF_3CH_2CHClCF_3$; 346mdf). Reacting $CF_3CHClCH_2CCl_3$ (343jfd) with HF is carried out in a liquid phase.

In some embodiments, the catalyst of step (b) is a metal halide. In some embodiments, the metal halide is $SbF_5$, $SbCl_5$, $SbCl_3$, $SnCl_4$, $TaCl_5$, $TiCl_4$, $NbCl_5$, $MoCl_6$, $WCl_6$, antimony (V) chlorofluorides, or combinations thereof. In some embodiments, the catalyst is $SbF_5$, $TaCl_5$, antimony (V) chlorofluorides, or combinations thereof. In some embodiments, the catalyst is $SbF_5$. In some embodiments, the catalyst is $TaCl_5$. In some embodiments, the catalyst is antimony (V) chlorofluorides.

In some embodiments, the catalyst of step (b) comprises between about 0.1% and about 20% by weight of the reaction mixture composition of step (b). For example, about 1% to about 15%, or about 5% to about 10%, or about 10% to about 15% by weight of the composition. In some embodiments, the catalyst comprises about 8% to about 10% or about 12% to about 15% by weight of the reaction mixture composition of step (b).

In some embodiments, the $CF_3CHClCH_2CCl_3$ (343jfd) can be present in the reaction mixture composition of step (b) in an amount of about 20% to about 50% by weight of the composition. For example, about 25% to about 45%, about 30% to about 40%, or about 32% to about 35% by weight of the reaction mixture composition of step (b).

In some embodiments, the HF can be present in the reaction mixture composition of step (b) in an amount of about 40% to about 70% by weight of the composition. For example, about 45% to about 65%, about 50% to about 60%, or about 52% to about 56% by weight of the reaction mixture composition of step (b).

In some embodiments, the reactants of step (b) can be added together at the same time. In some embodiments, the reactants of step (b) can be added together sequentially in any order. In some embodiments, the reactants of step (b) are added sequentially in the following order: (1) catalyst; (2) HF; (3) $CF_3CHClCH_2CCl_3$ (343jfd).

In some embodiments, after addition of the catalyst, the reaction mixture composition of step (b) is cooled to a temperature of about 0° C. to about 20° C., such as about 0° C., 5° C., 10° C., 15° C., or about 20° C. In some embodiments, after addition of the catalyst, the reaction mixture composition of step (b) is cooled to a temperature of about 0° C. to about 20° C. prior to addition of HF.

In some embodiments, after addition of HF, the reaction mixture composition of step (b) is heated to a temperature of about 90° C. to about 120° C., or about 100° C. to about 110° C., such as about 90° C., 95° C., 100° C., 105° C., 110° C., 115° C., or about 20° C. In some embodiments, the heating is performed for a time of about 30 minutes to about 5 hours or about 30 minutes, 1 hour, 2 hours, 3 hours, 4 hours, or about 5 hours. In some embodiments, the reaction mixture composition of step (b) is heated to a temperature of about 90° C. to about 120° C., or about 100° C. to about 110° C. for a time of about 30 minutes to about 5 hours. In some embodiments, after addition of HF, the reaction mixture composition of step (b) is heated to a temperature of about 90° C. to about 120° C. or about 100° C. to about 110° C. for a time of about 30 minutes to about 5 hours prior to addition of $CF_3CHClCH_2CCl_3$ (343jfd).

In some embodiments, after addition of HF, the reaction mixture composition of step (b) is cooled to a temperature of about 0° C. to about 20° C., such as about 0° C., 5° C., 10° C., 15° C., or about 20° C. In some embodiments, after addition of HF, the reaction mixture composition of step (b) is cooled to a temperature of about 0° C. to about 20° C. prior to addition of $CF_3CHClCH_2CCl_3$ (343jfd).

In some embodiments, after addition of HF, the reaction mixture composition of step (b) is heated to a temperature of about 90° C. to about 120° C. or about 100° C. to about 110° C. for a time of about 30 minutes to about 5 hours, followed by cooling to a temperature of about 0° C. to about 20° C. prior to addition of $CF_3CHClCH_2CCl_3$ (343jfd).

In some embodiments, after addition of $CF_3CHClCH_2CCl_3$ (343jfd), the reaction mixture composition of step (b) is heated to a temperature of about 50° C. to about 150° C., about 75° C. to about 130° C., or about 100° C. to about 115° C. In some embodiments, after addition of $CF_3CHClCH_2CCl_3$ (343jfd), the reaction mixture composition of step (b) is heated to a temperature of about 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., or about 150° C. In some embodiments, after addition of $CF_3CHClCH_2CCl_3$ (343jfd), the reaction mixture composition of step (b) is heated for a time of about 5 hours to about 30 hours or about 15 hours to about 25 hours. In some embodiments, after addition of $CF_3CHClCH_2CCl_3$ (343jfd), the reaction mixture composition of step (b) is heated for a time of about 5 hours, 10 hours, 15 hours, 20 hours, 24 hours, or about 30 hours. In some embodiments, after addition of $CF_3CHClCH_2CCl_3$ (343jfd), the reaction mixture composition of step (b) is heated to a temperature of about 50° C. to about 150° C., about 75° C. to about 130° C., or about 100° C. to about 115° C. for a time of about 5 hours to about 30 hours or about 15 hours to about 25 hours.

In some embodiments, the $CF_3CH_2CHClCF_3$ (346mdf) produced in the liquid phase reaction between $CF_3CHClCH_2CCl_3$ (343jfd) and HF in the presence of a catalyst is isolated prior to step (c). In some embodiments, $CF_3CH_2CHClCF_3$ (346mdf) is isolated with a purity of greater than about 90 mol %, 91 mol %, 92 mol %, 93 mol %, 94 mol %, 95 mol %, 96 mol %, 97 mol %, 98 mol %, or greater than about 99 mol %. In some embodiments, the purity is determined by chromatography. In some embodiments, the purity is determined by gas chromatography (GC) analysis.

In some embodiments, about 95% or greater of the $CF_3CHClCH_2CCl_3$ (343jfd) is converted to $CF_3CH_2CHClCF_3$ (346mdf) For example, about 95%, 96%, 97%, 98%, 99%, or 100% of the $CF_3CHClCH_2CCl_3$ (343jfd) is converted to $CF_3CH_2CHClCF_3$ (346mdf).

In some embodiments, in the liquid phase reaction between $CF_3CHClCH_2CCl_3$ (343jfd) and HF in the presence of a catalyst, the $CF_3CH_2CHClCF_3$ (346mdf) is produced in a yield of greater than about 90%, 91%, 92%, 93%, 94%, 95%, 96%, 97%, 98%, or 99%.

Step (c)—Production of $E-CF_3CH=CHCF_3$ (E-1336mzz)

In step (c), $CF_3CH_2CHClCF_3$ (346mdf) is treated with an effective amount of a base to form a mixture comprising the $E-CF_3CH=CHCF_3$ (E-1336mzz). Reacting $CF_3CH_2CHClCF_3$ (346mdf) with an effective amount of a base to form a mixture comprising the $E-CF_3CH=CHCF_3$ (E-1336mzz) is carried out in a liquid phase.

In some embodiments, the base of step (c) is an inorganic base. In some embodiments, the base of step (c) is lithium hydroxide, lithium oxide, sodium hydroxide, sodium oxide, potassium hydroxide, potassium oxide, rubidium hydroxide, rubidium oxide, cesium hydroxide, cesium oxide, calcium hydroxide, calcium oxide, strontium hydroxide, strontium oxide, barium hydroxide, and barium oxide. In some embodiments, the base is potassium hydroxide. In some embodiments, the base is sodium hydroxide.

In some embodiments, the base of step (c) is in an aqueous solution. In some embodiments, the concentration of base in the aqueous solution is about 1 M to about 12 M, or about 4 M to about 12 M, or about 5 M to about 10 M. In some embodiments, the concentration of base in the aqueous solution is about 5 M or about 10 M.

In some embodiments, the $CF_3CH_2CHClCF_3$ (346mdf) can be present in the reaction mixture composition of step (c) in an amount of about 20% to about 60% by weight of the composition. For example, about 25% to about 55%, about 30% to about 50%, or about 35% to about 45% by weight of the reaction mixture composition of step (c).

In some embodiments, step (c) is performed in the presence of a phase transfer catalyst. In some embodiments, the phase transfer catalyst is a quaternary ammonium salt, a heterocyclic ammonium salt, an organic phosphonium salt, or a nonionic compound. In some embodiments, the phase transfer catalyst is benzyltrimethylammonium chloride, benzyltriethylammonium chloride, methyltricaprylammonium chloride, methyltributylammonium chloride, methyltrioctylammonium chloride, dimethyldiphenylphosphonium iodide, methyltriphenoxyphosphonium iodide, tetrabutylphosphonium bromide, tetrabutylphosphonium chloride, hexadecyltributylphosphonium bromide, or DL-α-tocopherol methoxypolyethylene glycol succinate. In some embodiments, the phase transfer catalyst is methyltrioctylammonium chloride. An exemplary methyltrioctylammonium chloride phase transfer catalyst that is commercially available is Aliquat® 336 (Sigma Aldrich, St. Louis, Mo.).

In some embodiments, the phase transfer catalyst can be present in the reaction mixture composition of step (c) in an amount of about 0.01% to about 5% by weight of the composition. For example, about 0.1% to about 2.5%, about 0.5% to about 1.5%, or about 0.9% to about 1.3% by weight of the reaction mixture composition of step (c).

In some embodiments, reacting $CF_3CH_2CHClCF_3$ (346mdf) with an effective amount of a base to form a mixture comprising $E-CF_3CH=CHCF_3$ (E-1336mzz) is performed at a temperature of about 50° C. to about 100° C., about 60° C. to about 90° C., or about 60° C. to about 80° C. In some embodiments, reacting $CF_3CH_2CHClCF_3$ (346mdf) with an effective amount of a base to form a mixture comprising the $E-CF_3CH=CHCF_3$ (E-1336mzz) is performed at a temperature of about 50° C., 55° C., 60° C., 65° C., 70° C., 75° C., 80° C., 85° C., 90° C., 95° C., or about 100° C.

In some embodiments, reacting $CF_3CH_2CHClCF_3$ (346mdf) with an effective amount of a base to form a mixture comprising $E-CF_3CH=CHCF_3$ (E-1336mzz) is performed for a time of about 1 hour to about 10 hours or about 2 hours to about 5 hours. In some embodiments, reacting $CF_3CH_2CHClCF_3$ (346mdf) with an effective amount of a base to form a mixture comprising E-$CF_3CH=CHCF_3$ (E-1336mzz) is performed for a time of about 1 hour, 2 hours, 3 hours, 4 hours, 5 hours, 6 hours, 7 hours, 8 hours, 9 hours, or about 10 hours.

Reacting $CF_3CH_2CHClCF_3$ (346mdf) with an effective amount of a base to form a mixture comprising E-$CF_3CH=CHCF_3$ (E-1336mzz) can be performed at a temperature of about 50° C. to about 100° C., about 60° C. to about 90° C., or about 60° C. to about 80° C. for a time of about 1 hour to about 10 hours or about 2 hours to about 5 hours. In some embodiments, reacting $CF_3CH_2CHClCF_3$ (346mdf) with an effective amount of a base to form a mixture comprising E-$CF_3CH=CHCF_3$ (E-1336mzz) is performed at temperature of about 60° C. to about 80° C. for a time of about 1 hour to about 3 hours. In some embodiments, reacting $CF_3CH_2CHClCF_3$ (346mdf) with an effective amount of a base to form a mixture comprising E-$CF_3CH=CHCF_3$ (E-1336mzz) is performed at temperature of about 70° C. for a time of about 2 hours.

In some embodiments, reacting $CF_3CH_2CHClCF_3$ (346mdf) with an effective amount of a base to form a mixture comprising E-$CF_3CH=CHCF_3$ (E-1336mzz) also produces one or more of hexafluoroisobutylene (1336mt), 1,1,1,4,4,4-hexafluorobutane (356mff), (E)-1-chloro-1,1,4,4-pentafluorobut-2-ene (1335lzz), and Z—$CF_3CH=CHCF_3$.

In some embodiments, E-$CF_3CH=CHCF_3$ (E-1336mzz) is substantially isolated from the mixture. In some embodiments, E-$CF_3CH=CHCF_3$ (E-1336mzz) is formed with a yield of greater than about 90%, 92%, 94%, 95%, 96%, 97%, 98%, or 99%. In some embodiments, the yield of E-$CF_3CH=CHCF_3$ (E-1336mzz) is greater than 95%

In some embodiments, E-$CF_3CH=CHCF_3$ (E-1336mzz) is produced with a selectivity of greater than about 95 mol %, 96 mol %, 97 mol %, 98 mol %, or 99 mol % with respect to other components of the reaction mixture. In some embodiments, E-$CF_3CH=CHCF_3$ (E-1336mzz) is produced with a selectivity of about 99 mol % or greater with respect to other components of the reaction mixture.

Compositions

Also provided herein are compositions comprising E-$CF_3CH=CHCF_3$ (E-1336mzz). In some embodiments, the compositions comprise E-$CF_3CH=CHCF_3$ (E-1336mzz) and one or more additional compounds. In some embodiments, the composition comprises E-$CF_3CH=CHCF_3$ (E-1336mzz) and one or more additional components selected from hexafluoroisobutylene (1336mt), 1,1,1,4,4,4-hexafluorobutane (356mff), (E)-1-chloro-1,1,4,4-pentafluorobut-2-ene (1335lzz), and Z—$CF_3CH=CHCF_3$.

In some embodiments, the composition comprises greater than about 90 mol %, 91 mol %, 92 mol %, 93 mol %, 94 mol %, 95 mol %, 96 mol %, 97 mol %, 98 mol %, or greater than about 99 mol % E-$CF_3CH=CHCF_3$ (E-1336mzz). In some embodiments, the composition comprises greater than about 99 mol % E-$CF_3CH=CHCF_3$ (E-1336mzz).

Also provided herein are compositions prepared according to the process described herein. In some embodiments, the compositions prepared by the process described herein comprise E-$CF_3CH=CHCF_3$ (E-1336mzz). In some embodiments, the compositions prepared by the process described herein comprise E-$CF_3CH=CHCF_3$ (E-1336mzz) and one or more additional compounds. In some embodiments, the composition prepared by the process described herein comprises E-$CF_3CH=CHCF_3$ (E-1336mzz) and one or more additional components selected from hexafluoroisobutylene (1336mt), 1,1,1,4,4,4-hexafluorobutane (356mff), (E)-1-chloro-1,1,4,4-pentafluorobut-2-ene (1335lzz), and Z—$CF_3CH=CHCF_3$.

In some embodiments, the composition prepared by the process described herein comprises greater than about 90 mol %, 91 mol %, 92 mol %, 93 mol %, 94 mol %, 95 mol %, 96 mol %, 97 mol %, 98 mol %, or greater than about 99 mol % E-$CF_3CH=CHCF_3$ (E-1336mzz). In some embodiments, the composition prepared by the process described herein comprises greater than about 99 mol % E-$CF_3CH=CHCF_3$ (E-1336mzz).

EXAMPLES

The present disclosure is further defined in the following Examples. It should be understood that these Examples, while indicating preferred embodiments, are given by way of illustration only. From the above discussion and these Examples, one skilled in the art can ascertain the preferred features, and without departing from the spirit and scope thereof, can make various changes and modifications to adapt it to various uses and conditions.

Materials

Iron powder, carbon tetrachloride, Aliquat® 336 and sodium hydroxide were available from Sigma Aldrich, St. Louis, Mo. Hydrogen fluoride, $SbCl_5$ and 3,3,3-trifluoropropene were purchased from Synquest Labs, Inc.

Example 1: Preparation of 343jfd 3,3,3-trifluoropropene (66 g, 0.68 mol) was added to a mixture of carbon tetrachloride (158 g, 1.0 mol), Fe powder (1.12 g, 0.02 mol) and tributylphosphate (2.66, 0.01 mol) in a 400 mL Hastelloy Reactor. The reactor was heated to 110° C. for 3 hours. The mixture (217 g) was transferred to a container and analyzed by GC (100% 3,3,3-trifluoropropene conversion, 88% selectivity to 343jfd). The same reaction was repeated twice and all three batches of the material were combined. The subsequent fractionation provided 299 g of 98% pure $CCl_3CH_2CHClCF_3$ (343jfd). b.p. 92-94° C./140 torr. $^1H$ NMR (CDCl$_3$, 400 MHz) δ: 4.52 ($^1H$, q-d-d, $J^1=J^2=6.9$ Hz, $J^3=1.8$ Hz), 3.44 ($^1H$, d-d, $J^1=16.0$ Hz, $J^2=1.9$ Hz), 3.26 ($^1H$, d-d, $J^1=16.0$ Hz, $J^2=7.6$ Hz). $^{19}F$ NMR (CDCl$_3$, 376 MHz) δ: −74.85 (3F, d, J=6.9 Hz). MS (EI): 213 (M+-Cl).

Example 2: Preparation of 346mdf $SbF_5$ Catalyst

A 240 mL Hastelloy C vessel was charged with $SbF_5$ and cooled to 20° C. with dry ice/acetone. HF was added and the vessel was cooled and evacuated 3 times. $CCl_3CH_2CHClCF_3$ (343jfd) was added and the vessel was purged with $N_2$ three times. The reaction vessel was then heated to the desired temperature and shaken for 20 hours. 50 g ice water was added to quench the reaction. The product distribution was analyzed by GC and is shown in Table 1.

$TaCl_5$ Catalyst $TaCl_5$ (10.5 g) was added into a 210 mL Hastelloy C reactor, followed by HF addition (49 g). The reaction mixture was heated to 100° C. for 1 hour and then cooled to 0° C. $CCl_3CH_2CHClCF_3$ (343jfd) was added and the reaction was heated back to 100° C. for 20 hours. 50 g ice water was added to quench the reaction. The product distribution was analyzed by GC and is shown in Table 1.

TABLE 1

Product distribution

|  | 1 | 2 | 3 | 4 |
|---|---|---|---|---|
| Reactants |  |  |  |  |
| 343jfd | 30 g (0.12 mol) | 30 g (0.12 mol) | 30 g (0.12 mol) | 29 g (0.12 mol) |
| HF | 48 g (2.4 mol) | 48 g (2.4 mol) | 48 g (2.4 mol) | 49 g (2.4 mol) |
| Catalyst | SbF$_5$ - 8.0 g (0.037 mol) | SbF$_5$ - 8.0 g (0.037 mol) | SbF$_5$ - 8.0 g (0.037 mol) | TaCl$_5$ - 12.5 g (0.035 mol) |
| Products |  |  |  |  |
| E-1336mzz (%) | 1.6 | 0.2 | 2.1 | 4.3 |
| 346mdf (%) | 96.5 | 96.7 | 93.8 | 93.3 |
| 356mff | 0.2 | 0.1 | 0.2 | N/D |
| 1326mxz | 0.1 | 0.2 | 0.1 | N/D |
| 1336mt (%) | 0.01 | 0.01 | 0.01 | 0.01 |
| 345lfd | 0.7 | 1.8 | 2.0 | N/D |
| Unknown (%) | 0.9 | 1 | 1.8 | 2.4 |
| Temperature (° C.) | 50 | 75 | 100 | 130 |
| Conversion (%) | 100 | 100 | 100 | 100 |

$CF_3CH_2CHClCF_3$ (346mdf): b.p. 48-49° C. $^1$H NMR (CDCl$_3$, 400 MHz) δ: 4.36 ($^1$H, q-d-d, $J^1$=$J^2$=6.9 Hz, $J^3$=1.8 Hz), 2.90-2.80 ($^1$H, m), 2.72-2.61 ($^1$H, m). $^{19}$F NMR (CDCl$_3$, 376 MHz) δ: −64.84-−64.93 (3F, s), −76.17-−76.25 (3F, s). MS (EI): 200 (M+).

Example 3: Preparation of E-CF$_3$CH=CHCF$_3$ (E-1336mzz)

An aqueous solution of NaOH (6 mL, 0.06 mol) was added to 346mdf (10 g, 0.05 mol) and water (6.8 mL) at room temperature (RT) in the presence of 0.27 g of methyltrioctylammonium chloride (Aliquat® 336). The reaction temperature was raised to 70° C. after the addition, and gas chromatography was used to monitor the reaction. After 2 hours, 7.2 g of product E-CF$_3$CH=CHCF$_3$ (E-1336mzz) was collected in a dry ice trap (E-1336mzz selectivity 99.4%, yield: 95.4%).

Example 4: Preparation of E-CF$_3$CH=CHCF$_3$(E-1336mzz)

An aqueous solution of KOH (6 mL, 0.06 mol) was added to 346mdf (10 g, 0.05 mol) and water (6.8 mL) at room temperature (RT). The reaction temperature was raised to 70° C. after the addition, and gas chromatography was used to monitor the reaction. After 2 hours, 7.6 g of product E-CF$_3$CH=CHCF$_3$ (E-1336mzz) was collected in a dry ice trap (E-1336mzz selectivity 99.5%, yield: 96%).

The product composition is shown in Table 2, below, and contains greater than 99% E-1336mzz.

TABLE 2

Product composition

| Products |
|---|
| E-1336mzz (E—CF$_3$CH=CHCF$_3$) |
| Z-1336mzz (Z—CF$_3$CH=CHCF$_3$) |
| 1336mt (CF$_3$(CF$_3$)C=CH$_2$) |
| 356mff (CF$_3$CH$_2$CH$_2$CF$_3$) |
| 1335lzz (CF$_2$ClCH=CHCF$_3$) |

Comparative Example: Preparation of E-CF$_3$CH=CHCF$_3$(E-1336mzz)

An aqueous solution of NaOH (6 mL, 0.06 mol) was added to 346mdf (10 g, 0.05 mol) and water (6.8 mL) at room temperature (RT). The reaction temperature was raised to 70° C. after the addition, and gas chromatography was used to monitor the reaction. After 2 hours, 0.1 g of product E-CF$_3$CH=CHCF$_3$ (E-1336mzz) was collected in a dry ice trap (yield: <1%).

OTHER EMBODIMENTS

1. In some embodiments, the present application provides a process for preparing E-CF$_3$CH=CHCF$_3$, comprising:
   treating CF$_3$CH$_2$CHClCF$_3$ with an effective amount of a base to form a mixture comprising the E-CF$_3$CH=CHCF$_3$, wherein the process is a liquid phase process.

2. In some embodiments, the present application provides a process for preparing E-CF$_3$CH=CHCF$_3$, comprising:
   treating CF$_3$CH$_2$CHClCF$_3$ with an effective amount of a base to form a mixture comprising the E-CF$_3$CH=CHCF$_3$ and one or more of hexafluoroisobutylene (1336mt), 1,1,1,4,4,4-hexafluorobutane (356mff), (E)-1-chloro-1,1,4,4,4-pentafluorobut-2-ene (1335lzz), and Z—CF$_3$CH=CHCF$_3$, wherein the process is a liquid phase process.

3. The process of embodiment 1 or 2, wherein the base is selected from the group consisting of lithium hydroxide, lithium oxide, sodium hydroxide, sodium oxide, potassium hydroxide, potassium oxide, rubidium hydroxide, rubidium oxide, cesium hydroxide, cesium oxide, calcium hydroxide, calcium oxide, strontium hydroxide, strontium oxide, barium hydroxide, and barium oxide.

4. The process of embodiment 1 or 2, wherein the base is potassium hydroxide.

5. The process of embodiment 1 or 2, wherein the base is sodium hydroxide.

6. The process of any one of embodiments 1 to 5, wherein the base is in an aqueous solution.

7. The process of embodiment 6, wherein the concentration of base in the aqueous solution is from about 4 M to about 12 M.

8. The process of any one of embodiments 1 to 7, wherein the process is performed in the presence of a phase transfer catalyst.

9. The process of embodiment 8, wherein the phase transfer catalyst is selected from the group consisting of a quaternary ammonium salt, a heterocyclic ammonium salt, an organic phosphonium salt, and a nonionic compound.

10. The process of embodiment 8 or 9, wherein the phase transfer catalyst is selected from the group consisting of benzyltrimethylammonium chloride, benzyltriethylammonium chloride, methyltricaprylammonium chloride, methyltributylammonium chloride, methyltrioctylammonium chloride, dimethyldiphenylphosphonium iodide, methyltriphenoxyphosphonium iodide, tetrabutylphosphonium bromide, tetrabutylphosphonium chloride, hexadecyltributylphosphonium bromide, and DL-α-tocopherol methoxypolyethylene glycol succinate.

11. The process of embodiment 8 or 9, wherein the phase transfer catalyst is methyltrioctylammonium chloride.

12. The process of embodiment 8 or 9, wherein the base is sodium hydroxide and the phase transfer catalyst is methyltrioctylammonium chloride.

13. The process of any one of embodiments 1 to 12, wherein the mixture further comprises one or more of hexafluoroisobutylene (1336mt), 1,1,1,4,4,4-hexafluorobutane (356mff), (E)-1-chloro-1,1,4,4,4-pentafluorobut-2-ene (1335lzz), and Z—$CF_3CH=CHCF_3$.

14. The process of any one of embodiments 1 to 13, wherein the E-$CF_3CH=CHCF_3$ is produced in a yield of about 95% or greater.

15. The process of any one of embodiments 1 to 13, wherein the E-$CF_3CH=CHCF_3$ is produced with a selectivity of about 99 mol % or greater with respect to other components of the mixture.

16. The process of any one of embodiments 1 to 13, wherein the E-$CF_3CH=CHCF_3$ is substantially isolated from the mixture.

17. The process of any one of embodiments 1 to 13, wherein the $CF_3CH_2CHClCF_3$ is prepared according to a second process comprising contacting $CF_3CHClCH_2CCl_3$ with HF in the presence of a catalyst, wherein the second process is a liquid phase process.

18. The process of embodiment 17, wherein the catalyst is a metal halide.

19. The process of embodiment 18, wherein the metal halide is selected from the group consisting of $SbF_5$, $SbCl_5$, $SbCl_3$, $SnCl_4$, $TaCl_5$, $TiCl_4$, $NbCl_5$, $MoCl_6$, $WCl_6$, antimony (V) chlorofluorides, and combinations thereof.

20. The process of embodiment 18, wherein the metal halide is $SbF_5$.

21. The process of embodiment 18, wherein the metal halide is $TaCl_5$.

22. The process of embodiment 18, wherein the metal halide is antimony (V) chlorofluorides.

23. The process of any one of embodiments 17 to 22, wherein the second process is performed at a temperature of from about 50° C. to about 100° C.

24. The process of any one of embodiments 17 to 23, wherein the $CF_3CH_2CHClCF_3$ is produced in a yield of about 93% or greater.

25. The process of any one of embodiments 17 to 24, wherein the $CF_3CH_2CHClCF_3$ is produced in a yield of about 95% or greater.

26. The process of any one of embodiments 17 to 25, wherein the $CF_3CHClCH_2CCl_3$ is prepared by a third process comprising contacting carbon tetrachloride with 3,3,3-trifluoropropene in the presence of an organophosphorus compound and a catalyst comprising a metal, wherein the third process is a liquid phase process.

27. The process of embodiment 26, wherein the organophosphorus compound is selected from the group consisting of a phosphate ester, a phosphate amide, a phosphonic acid, a phosphonic ester, a phosphinic acid, a phosphinic ester, a phosphine oxide, a phosphine imide, a phosphonium salt, a phosphorene, a phosphite, a phosphonate, a phosphinite, and a phosphine.

28. The process of embodiment 26 or 27, wherein the organophosphorus compound is selected from the group consisting of a phosphate, a diphosphate, a triphosphate, and a trialkylphosphate.

29. The process of any one of embodiments 26 to 28, wherein the organophosphorus compound is tributylphosphate.

30. The process of any one of embodiments 26 to 29, wherein the metal of the catalyst of the third process is selected from the group consisting of Fe, Co, Ni, Cu, Mo, Cr, and Mn.

31. The process of any one of embodiments 26 to 29, wherein the metal of the catalyst of the third process is Fe.

32. The process of any one of embodiments 26 to 29, wherein the third process takes place at a temperature of from about 100° C. to about 120° C.

33. In some embodiments, the present application further provides a process for preparing E-$CF_3CH=CHCF_3$, comprising:
(a) contacting carbon tetrachloride with 3,3,3-trifluoropropene in the presence of an organophosphorus compound and a catalyst comprising a metal to produce $CF_3CHClCH_2CCl_3$;
(b) contacting the $CF_3CHClCH_2CCl_3$ with HF in the presence of a catalyst to produce $CF_3CH_2CHClCF_3$; and
(c) treating the $CF_3CH_2CHClCF_3$ with an effective amount of a base to form a mixture comprising the E-$CF_3CH=CHCF_3$,
wherein the process is a liquid phase process.

34. The process of embodiment 33, wherein step (c) is performed in the presence of a phase transfer catalyst.

35. The process of embodiment 33, wherein the mixture of step (c) further comprises one or more of hexafluoroisobutylene (1336mt), 1,1,1,4,4,4-hexafluorobutane (356mff), (E)-1-chloro-1,1,4,4,4-pentafluorobut-2-ene (1335lzz), and Z—$CF_3CH=CHCF_3$.

36. In some embodiments, the present application further provides a process for preparing E-$CF_3CH=CHCF_3$, comprising:
(a) contacting carbon tetrachloride with 3,3,3-trifluoropropene in the presence of an organophosphorus compound and a catalyst comprising a metal to produce $CF_3CHClCH_2CCl_3$;
(b) contacting the $CF_3CHClCH_2CCl_3$ with HF in the presence of a catalyst to produce $CF_3CH_2CHClCF_3$; and
(c) treating the $CF_3CH_2CHClCF_3$ with an effective amount of a base in the presence of a phase transfer catalyst to form a mixture comprising the E-$CF_3CH=CHCF_3$,
wherein the process is a liquid phase process.

37. The process of embodiment 36, wherein the base of step (c) is sodium hydroxide.

38. The process of embodiment 36 or 37, wherein the mixture of step (c) further comprises one or more of hexafluoroisobutylene (1336mt), 1,1,1,4,4,4-hexafluorobutane (356mff), (E)-1-chloro-1,1,4,4,4-pentafluorobut-2-ene (1335lzz), and Z—$CF_3CH=CHCF_3$.

39. The process of any one of embodiments 36 to 38, wherein the E-$CF_3CH=CHCF_3$ is substantially isolated from the mixture.

40. In some embodiments, the present application further provides a composition comprising:
E-$CF_3CH=CHCF_3$; and
one or more additional compounds selected from the group consisting of hexafluoroisobutylene (1336mt), 1,1,1,4,4,4-hexafluorobutane (356mff), (E)-1-chloro-1,1,4,4,4-pentafluorobut-2-ene (1335lzz), and Z—$CF_3CH=CHCF_3$,
wherein the composition comprises greater than about 99 mol % E-$CF_3CH=CHCF_3$.

41. In some embodiments, the present application further provides a composition prepared according to any of the processes provided herein, the composition comprising:
E-$CF_3CH=CHCF_3$; and
one or more additional compounds selected from the group consisting of hexafluoroisobutylene (1336mt), 1,1,1,4,4,4-hexafluorobutane (356mff), (E)-1-chloro-1,1,4,4,4-pentafluorobut-2-ene (1335lzz), and Z—$CF_3CH=CHCF_3$,
wherein the composition comprises greater than about 99 mol % E-$CF_3CH=CHCF_3$.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

What is claimed is:

1. A process for preparing E-$CF_3CH\!=\!CHCF_3$, comprising:
   treating $CF_3CH_2CHClCF_3$ with an effective amount of a base in the presence of a phase transfer catalyst and a solvent component consisting of water, to form a mixture comprising the E-$CF_3CH\!=\!CHCF_3$,
   wherein the process is a liquid phase process and the base is sodium hydroxide.

2. The process of claim 1, wherein the mixture further comprises one or more of hexafluoroisobutylene, 1,1,1,4,4,4-hexafluorobutane, (E)-1-chloro-1,1,4,4,4-pentafluorobut-2-ene, and Z—$CF_3CH\!=\!CHCF_3$.

3. The process of claim 1, wherein the base is in an aqueous solution of from about 4 M to about 12 M.

4. The process of claim 1, wherein the phase transfer catalyst is selected from the group consisting of a quaternary ammonium salt, a heterocyclic ammonium salt, an organic phosphonium salt, and a nonionic compound.

5. The process of claim 4, wherein the phase transfer catalyst is selected from the group consisting of benzyltrimethylammonium chloride, benzyltriethylammonium chloride, methyltricaprylammonium chloride, methyltributylammonium chloride, methyltrioctylammonium chloride, dimethyldiphenylphosphonium iodide, methyltriphenoxyphosphonium iodide, tetrabutylphosphonium bromide, tetrabutylphosphonium chloride, hexadecyltributylphosphonium bromide, and DL-α-tocopherol methoxypolyethylene glycol succinate.

6. The process of claim 5, wherein the phase transfer catalyst is methyltrioctylammonium chloride.

7. The process of claim 4, wherein the base is sodium hydroxide and the phase transfer catalyst is methyltrioctylammonium chloride.

8. The process of claim 1, wherein the E-$CF_3CH\!=\!CHCF_3$ is substantially isolated from the mixture.

9. The process of claim 1, wherein the $CF_3CH_2CHClCF_3$ is prepared according to a second process comprising contacting $CF_3CHClCH_2CCl_3$ with HF in the presence of a catalyst, wherein the second process is a liquid phase process.

10. The process of claim 9, wherein the catalyst is a metal halide selected from the group consisting of $SbF_5$, $SbCl_5$, $SbCl_3$, $SnCl_4$, $TaCl_5$, $TiCl_4$, $NbCl_5$, $MoCl_6$, $WC_{16}$, antimony (V) chlorofluorides, and combinations thereof.

11. The process of claim 10, wherein the metal halide is selected from the group consisting of $SbF_5$, $TaCl_5$, and antimony (V) chlorofluorides.

12. The process of claim 9, wherein the second process is performed at a temperature of from about 50° C. to about 100° C.

13. The process of claim 9, wherein the $CF_3CHClCH_2CCl_3$ is prepared by a third process comprising contacting carbon tetrachloride with 3,3,3-trifluoropropene in the presence of an organophosphorus compound and a catalyst comprising a metal, wherein the third process is a liquid phase process.

14. The process of claim 13, wherein the organophosphorus compound is selected from the group consisting of a phosphate ester, a phosphate amide, a phosphonic acid, a phosphonic ester, a phosphinic acid, a phosphinic ester, a phosphine oxide, a phosphine imide, a phosphonium salt, a phosphorene, a phosphite, a phosphonate, a phosphinite, and a phosphine.

15. The process of claim 14, wherein the organophosphorus compound is tributylphosphate.

16. The process of claim 13, wherein the metal of the catalyst is selected from the group consisting of Fe, Co, Ni, Cu, Mo, Cr, and Mn.

17. The process of claim 16, wherein the metal is Fe.

18. The process of claim 13, wherein the third process takes place at a temperature of from about 100° C. to about 120° C.

19. A process for preparing E-$CF_3CH\!=\!CHCF_3$, comprising:
   (a) contacting carbon tetrachloride with 3,3,3-trifluoropropene in the presence of an organophosphorus compound and a catalyst comprising a metal to produce $CF_3CHClCH_2CCl_3$;
   (b) contacting the $CF_3CHClCH_2CCl_3$ with HF in the presence of a catalyst to produce $CF_3CH_2CHClCF_3$; and
   (c) treating the $CF_3CH_2CHClCF_3$ with an effective amount of a base in the presence of a phase transfer catalyst and a solvent component consisting of water, to form a mixture comprising the E-$CF_3CH\!=\!CHCF_3$,
   wherein the process is a liquid phase process, and the base of step (c) is sodium hydroxide.

20. The process of claim 19, wherein the mixture of step (c) further comprises one or more of hexafluoroisobutylene, 1,1,1,4,4,4-hexafluorobutane, (E)-1-chloro-1,1,4,4,4-pentafluorobut-2-ene, and Z—$CF_3CH\!=\!CHCF_3$.

21. The process of claim 19, wherein the E-$CF_3CH\!=\!CHCF_3$ is substantially isolated from the mixture.

22. A composition, consisting of comprising:
   E-$CF_3CH\!=\!CHCF_3$,
   hexafluoroisobutylene, 1,1,1,4,4,4-hexafluorobutane, (E)-1-chloro-1,1,4,4,4-pentafluorobut-2-ene, and Z—$CF_3CH\!=\!CHCF_3$.

23. The composition of claim 22, wherein the composition consists of greater than about 99 mol % E-$CF_3CH\!=\!CHCF_3$.

24. The composition of claim 22, which is prepared according to a process comprising treating $CF_3CH_2CHClCF_3$ with an effective amount of a base in the presence of a phase transfer catalyst and a solvent component consisting of water, wherein the process is a liquid phase process and the base is sodium hydroxide.

* * * * *